United States Patent [19]
Saeki et al.

[11] Patent Number: 5,885,830
[45] Date of Patent: Mar. 23, 1999

[54] ANTI-RIBONUCLEOTIDE REDUCTASE R2 SUBUNIT MONOCLONAL ANTIBODY

[75] Inventors: Toshiaki Saeki, Matsuyama; Toshiaki Kamei, Hofu; Akiko Furuya, Machida; Nobuo Hanai, Sagamihara; Takeshi Takahashi, Sunto-gun; Masami Okabe, Mishima; Motoo Yamasaki, Machida, all of Japan

[73] Assignee: Kyowa Hakko Kogyo Co., Ltd., Tokyo, Japan

[21] Appl. No.: 597,803

[22] Filed: Feb. 7, 1996

[30] Foreign Application Priority Data

Feb. 7, 1995 [JP] Japan ................................ 7-018879

[51] Int. Cl.$^6$ .............................. C07K 16/18; C12N 5/12; G01N 33/53
[52] U.S. Cl. ......................... 435/326; 435/330; 435/332; 435/338; 435/7.1; 435/7.21; 435/7.23; 530/388.2; 530/388.26; 530/388.8; 530/388.85
[58] Field of Search .......................... 530/388.26, 388.2, 530/388.8, 388.85; 435/7.1, 7.23, 7.4, 7.21, 326, 330, 332, 338

[56] References Cited

PUBLICATIONS

Biochemistry, vol. 25, No. 4, 1986, pp. 860–867, A. Anderson, et al., "Production and characterization of monoclonal antibodies against two subunits proteins B1 and B2 of *Escherichia Coli* Ribonucleotide reductase".

Biochemistry and Cell Biology, vol. 70, 1992, pp. 1081–1087, R.A.R. Hurta & J.A. Wright, "regulation of mammalian ribonucleotide reductase by tumor promoters and protein phosphatase inhibitors okadaic acid and calyculin A".

J. Clin. Invest., vol. 87, 1991, pp. 519–527, D.L.M. Tay et al., "Quantitation of G0 and G1 phase cells in primary carcinomas".

International Journal of Oncology, vol. 6, Mar. 1995, pp. 523–529, T. Saeki, et al., "Immunohistochemical detection of ribonucleotide reductase in human breast tumors".

Thelander, et al., "Reduction of Ribonucleotides", *Annu. Rev. Biochem.*; vol. 48, pp. 133–158 (1979).

Eriksson, et al., "Ribonucleotide Reductase in Cultured Mouse Lymphoma Cells", *The Journal of Biological Chemistry*, vol. 256 No. 18, pp. 9436–9440 (1981).

Engstrom, et al., "Immunocytochemical evidence for the cytoplasmic localization and differential expression during the cell cycle of the M1 and M2 subunits of mammalian ribonucleotide reductase", *The EMBO Journal*, vol. 7, No. 6, pp. 1615–1620 (1988).

Yano, et al., Inhibition of Histamine Secretion by Wortmannin through the Blockade of Phosphatidylinositol 3–Kinase in RBL–2H3 Cells, *Journal of Biological Chemistry*, vol. 268, No. 34, pp. 25846–25856 (1993).

Takeda, et al., "Role of Ribonucleotide Reductase in Expression of the Neoplastic Program", *Life Sciences*, vol. 28, pp. 1007–1014 (1981).

Streeper, et al., "A Rapid Assay for CDP Reductase Activity in Mammalian Cell Extracts", *Analytical Biochemistry*, vol. 34, pp. 123–130 (1970).

Engstrom, "Monoclonal Antibodies Against Mammalian Ribonucleotide Reductase", *Acta Chemica Scandinavia*, vol. B36, No. 5, pp. 343 and 344.

Cosentino et al, Biochem Cell Biol 69:79–83, 1991.

*Primary Examiner*—Toni R. Scheiner
*Assistant Examiner*—Nancy A. Johnson
*Attorney, Agent, or Firm*—Antonelli, Terry, Stout & Kraus, LLP

[57] ABSTRACT

An anti-ribonucleotide reductase (RNR) R2 subunit monoclonal antibody KM1054, KM1056 or KM1060, which belongs to the IgG2a subclass, reacts with R2 subunit of RNR, and inhibits RNR activity, is disclosed. It is effective for immunologically detecting RNR and for immunologically detecting the presence of human cancer cells.

7 Claims, 8 Drawing Sheets

HUMAN PERIPHERAL BLOOD LYMPH BLAST

ANTI-RIBONUCLEOTIDE REDUCTASE R2 SUBUNIT MONOCLONAL ANTIBODY

BACKGROUND OF THE INVENTION

The present invention relates to a monoclonal antibody which is specifically reactive with a ribonucleotide reductase R2 subunit and which inhibits ribonucleotide reductase activity, as well as a hybridoma cell line producing the monoclonal antibody. The present invention further relates to a method of immunologically detecting a ribonucleotide reductase R2 subunit using the monoclonal antibody.

A ribonucleotide reductase (hereinafter referred to as "RNR") is an enzyme catalyzing the reduction of ribonucleoside diphosphate into deoxyribonucleoside diphosphate which is a part in DNA. Since RNR activity is strongly correlated with a cell proliferation rate and since deoxyribonucleotide is reluctant to pool in cells, RNR controls a rate-determining step of DNA synthesis (Annu. Rev. Biochem., 48, 133–158, 1979), and can be considered as a cell cycle marker and a proliferation marker. In fact, it is known that RNR activity increases or decreases depending on the cell cycle, and that the level of RNR activity is lower at G0/G1 phase and is the highest at S phase. RNR is composed of two subunits R1 and R2, either of which does not individually have any activity at all. It is reported that since the R1 subunit is always expressed constantly and sufficiently, RNR activity is controlled by the amount of the R2 subunit expressed, which amount depends on the cell cycle [J.B.C., 256 (18), 9436–9440, 1981]. It is further reported that the level of RNR activity is higher in human tumor tissue than in human normal tissue (Life Science, 28, 1007–1014, 1981), and that RNR can be utilized as a tumor marker and a tumor proliferation marker.

A conventional method of determining RNR activity (Analytical Biochemistry, 34, 123–130, 1970) is not satisfactory because of the difficulty in determining the activity of RNR scattered in a tissue. A simple and accurate method of detecting RNR has been in demand.

An anti-RNR monoclonal antibody which is reactive with an R1 subunit and which inhibits RNR activity has been known [Acta Chem. Scand., B36 (5), 343, 1982]. A monoclonal antibody which is reactive with an R2 subunit has been known [The EMBO Journal, 7 (6), 1615, 1988)]. But the known monoclonal antibody which is reactive with R2 subunit does not inhibit RNR activity.

An object of the present invention is to provide a monoclonal antibody which is specifically reactive with an R2 subunit of human RNR, and which inhibits RNR activity.

The monoclonal antibody of the present invention is a neutral antibody against RNR, and thus it inhibits the RNR activity dependent on the concentrations of the monoclonal antibody.

By Western blotting and immunoprecipitation using the present monoclonal antibody, it is found that the present monoclonal antibody is reactive with a protein having a molecular weight of 45K daltons which coincides with the molecular weight of the R2 subunit of RNR. Further, by the immunological staining of culture cells and various human tissues using the present monoclonal antibody, it is found that the monoclonal antibody can specifically detect RNR in the cells and human tissues.

The monoclonal antibody of the present invention is useful not only for immunologically detecting a R2 subunit of RNR in tissues and cells, but also for studying the biological characterization of RNR. Thus, it is expected that the fundamental study of cancer will be promoted by analysis of RNR.

SUMMARY OF THE INVENTION

According to the present invention, there is provided a monoclonal antibody selected from the group consisting of KM1054, KM1056 and KM1060 which is specifically reactive with a R2 subunit of RNR (hereinafter referred to as RNR·R2 subunit) and which inhibits RNR activity. As the hybridoma producing the monoclonal antibody of the present invention, hybridoma cell lines KM1054, KM1056 and KM1060 are mentioned.

Further, according to the present invention, there is provided a method of immunologically detecting RNR·R2 subunit, as well as a method of immunologically detecting the presence of human cancer cells, using the monoclonal antibody of the present invention.

DETAILED DESCRIPTION OF THE INVENTION

The present invention provides the monoclonal antibody obtained by fusing spleen cells of a rat immunized with a C-terminal peptide of an R2 subunit of human RNR preparation and murine myeloma cell lines to generate hybridomas, selecting from among the hybridomas obtained a hybridoma clone producing a monoclonal antibody having specificity to an RNR·R2 subunit and cultivating the selected hybridoma clone in a medium or administering the hybridoma clone to a mouse to thereby cause hybridoma cell propagation in the ascitic fluid in the mouse.

More specifically, the process for producing the monoclonal antibody of the present invention is described below.
(1) Immunization of animals and preparation of antibody-producing cells As the antigen, a peptide which is bound to a carrier protein such as keyhole lympet hemocyanin (hereinafter referred to as "KLH") and bovine serum albumin (hereinafter referred to as "BSA") with a crosslinking agent such as glutaraldehyde and N-(m-maleimidebenzoyloxy) succinimide (hereinafter referred to as "MBS"), is used.

Mice or rats of 3 to 20 weeks of age are immunized with a R2 subunit C-terminal peptide of human RNR having the amino acid sequence shown in SEQ. ID NO:1 bound to the above-mentioned carrier protein, and antibody-producing cells are collected from the spleen, lymph node or peripheral blood of the animals.

The immunization is performed generally by administering the antigen in combination with a suitable adjuvant for example, complete Freund's adjuvant, and an aluminum hydroxide gel plus Pertussis vaccine, to the animals subcutaneously, intravenously or intraperitoneally.

The antigen is administered repeatedly 5 to 10 times at one or two week intervals following the first antigen administration. 3 to 7 days after each administration, blood is sampled from the venous plexus of the fundus of the eye, and the serum derived from the sample blood is tested as to whether it is reactive with the antigen by enzyme-linked immunosorbent assay (ELISA: Report published in Igaku Shoin, 1976).

The mice or rat whose serum exhibits a sufficient antibody titer against the peptide used for immunization is submitted as a source of antibody-producing cells.

In the fusion of the antibody-producing cells and the myeloma cells, the spleen cells are used as the antibody-producing cells. The spleen of the immunized mouse is excised 3 to 7 days after the final administration of the antigen, and the spleen cells are collected therefrom. The spleen is cut to pieces in a minimal essential medium (MEM) (made by Nissui Pharmaceutical), and loosened by means of a pincette. After centrifugation at 1,200 rpm for 5 minutes, the supernatant is then discarded, and the residue is treated with a tris-ammonium chloride buffer (pH 7.65) for 1 to 2 minutes to remove erythrocytes. The residual cells are washed with MEM three times, and are used as splenocytes for cell fusion.

(2) Preparation of myeloma cells

As myeloma cells, a cell line obtained from a mouse is used. For instance, 8-azaguanine-resistant mouse (derived from BALB/c) myeloma cell lines, P3-X63Ag8-U1 (P3-U1) [Current Topics in Microbiology and Immunology, 81, 1–7 (1978), and European J. Immunology, 6, 511–519 (1976)], SP2/0-Ag14 (SP-2) [Nature, 276, 269–270 (1978)], P3-X63-Ag8653 (653) [J. Immunology, 123, 1548–1550 (1979)] and P3-X63-Ag8 (X63) [Nature, 256, 495–497 (1975)] may be used. These cell lines are cloned in an 8-azaguanine medium RPMI-1640 [medium with glutamine (1.5 mM), 2-mercaptoethanol ($5 \times 10^{-5}$M), gentamicin (10 µg/ml) and fetal calf serum (FCS) (CSL; 10%) and further supplementing the resulting normal medium (hereinafter "the normal medium") with 8-azaguanine (15 µg/ml)]. These cell lines are cloned in the normal medium 3 to 4 days before cell fusion, and at least $2 \times 10^7$ cells are secured on the day of the fusion.

(3) Cell fusion

The antibody-producing cells obtained in (1) and the myeloma cells obtained in (2) are washed well with MEM or PBS (containing 1.83 g of sodium dihydrogen phosphate, 0.21 g of potassium monohydrogen phosphate, 7.65 g of sodium chloride and 1 liter of distilled water, pH 7.2), and are mixed until the ratio of the antibody-producing cells to the myeloma cells is rendered 5–10:1. The cell mixture is subjected to centrifugation at 1,200 rpm for 5 minutes, and the supernatant is then discarded. The pellet is suspended, and 0.2 to 1 ml, per $10^8$ of the antibody-producing cells, of a mixed solution containing 2 g of polyethylene glycol-1, 000 (PEG-1,000), 2 ml of MEM and 0.7 ml of dimethyl sulfoxide is added to the suspension at 37° C. with stirring. Then, 1 to 2 ml of MEM are added several times every 1 to 2 minutes. Thereafter, the whole amount of MEM is made 50 ml by further addition of MEM. The mixture is centrifuged at 900 rpm for 5 minutes, and the supernatant is discarded. The pellet is gently loosened, and then suspended by means of a pipette in 100 ml of HAT medium [medium prepared by adding $10^{-4}$M hypoxanthine, $1.5 \times 10^{-5}$M thymidine and $4 \times 10^{-7}$M aminopterin to the normal medium] while the cells are sucked in and out by means of a measuring pipette. The suspension is distributed in 100 µl/well portion, on a 96-well culture plate, and incubation is carried out in a 5% $CO_2$ incubator at 37° C. for 7 to 14 days.

After the incubation, a portion of the culture supernatant in each well is sampled to select the well in which specific reactivity with a C-terminal peptide of a R2 subunit of human RNR is higher. Then, the cloning is repeated twice through limiting dilution in which a HT medium prepared by removing aminopterin from a HAT medium is used in the first dilution, and the normal medium is used in the second dilution. The cell line which is found to have a stable strong antibody titer is selected as a hybridoma cell line producing an anti-RNR·R2 subunit monoclonal antibody. Specific examples of the competent hybridoma cell line include hybridoma cell lines KM1054, KM1056 and KM1060. Hybridoma cell line KM1054 has been deposited at the National Institute of Bioscience and Human Technology of the Agency of Industrial Science and Technology 1–3, Higashi 1-chome, Tsukuba-shi, Ibaraki-ken, 305 Japan as FERM BP-4875 as from Nov. 8, 1994.

Enzyme immunoassay

As an antigen, the C-terminal peptide of the R2 subunit of RNR is used. The peptide is bound to a protein different from that used in the immunization as a carrier protein and a crosslinking agent such as glutaraldehyde and MBS.

The conjugate (from 1 to 50 µg/ml) of the C-terminal peptide of the R2 subunit of human RNR and the carrier protein is distributed in an amount of 10 to 100 µl/well, and the plate is kept at 4° C. for 10 hours for coating. After the blocking with a BSA solution, the hybridoma culture supernatant is added in an amount of 50 to 100 µl/well as a first antibody, and the reaction is conducted at room temperature for 2 hours or at 4° C. for 10 hours. The EIA plate is washed well with PBS or a solution of PBS in 0.05% Tween-20 (hereinafter referred to as "Tween-PBS"). Then, 1 to 50 µg/ml of an anti-mouse immunoglobulin antibody or an anti-rat immunoglobulin antibody which is labeled with biotin, an enzyme, a chemiluminescent substance or a radioactive compound, is added in an amount of 50 to 100 µl/well as a second antibody, and the reaction is conducted at room temperature for 1 to 2 hours. After the EIA plate is washed well, the reaction is conducted depending on the labelling substance for the second antibody. The well in which specific reactivity with the C-peptide of the R2 subunit of human RNR is higher, is selected as a hybridoma producing the anti-RNR·R2 subunit monoclonal antibody.

(4) Preparation of a monoclonal antibody

The anti-RNR·R2 subunit monoclonal antibody-producing hybridoma cell lines obtained in (3) are intraperitoneally administered into 8- to 10-week-old mice or nude mice treated with pristane [0.5 ml of 2,6,10,14-tetramethylpentadecane (pristane) has intraperitoneally been administered to the mice and the mice have been maintained for two weeks] in amounts of from $2\times10^7$ to $5\times10^6$ cells/mouse. In 10 to 21 days, the hybridoma cells produce ascitic carcinoma in the mice. The ascitic fluid is collected from the mice, and centrifuged at 3,000 rpm for 5 minutes to remove the solid matters. The residue is then salted out from a 40 to 50% saturated solution of ammonium sulfate, and is subjected to caprylic-acid precipitation to give a purified monoclonal antibody. Alternatively, the residue is passed through a DEAE-sepharose column, a protein A column or Cellulofine GSL 2000 (manufactured by Seikagaku Corp.) column, and an IgG or IgM fraction is collected and used as a purified monoclonal antibody.

The subclass of the antibody is determined using a mouse monoclonal antibody typing kit (Zymed Laboratories) or a rat monoclonal antibody typing kit (Nordic Immunology). The amount of the protein is determined by the Lowry method or from the absorbance of 280 nm.

(5) Examination of specificity of the monoclonal antibody by the Western blotting The reaction specificity of the anti-RNR·R2 subunit monoclonal antibody obtained in (4) is examined by the following Western blotting.

First, a RNR crude fraction is prepared from a human tumor cell line such as HelaS$_3$, as follows.

A homogenate is prepared from human tumor cells, and centrifuged to collect the supernatant. Streptomycin sulfate is added until the final concentration reaches 0.65% (w/v), and the mixture is stirred at 4° C. for 30 minutes. The reaction mixture is centrifuged to collect a supernatant. Then, ammonium sulfate is added until the final concentration reaches 50% saturation. The mixture is stirred at 4° C. for 45 minutes, and then centrifuged to collect a precipitate. The precipitate is dissolved in a tris-hydrochloride buffer comprising 50 mM tris-hydrochloride (tris-HCl)(pH 7.6), 0.1 mM phenylmethanesulfonyl fluoride (PMSF) and 2 mM dithiothreitol (DTT), and the solution is further dialyzed against the tris-hydrochloride buffer for 10 hours. The resulting dialyzate is used as a RNR crude fraction.

The thus-obtained RNR crude fraction is fractionated through SDS polyacrylamide gel electrophoresis (SDS-PAGE), and is then blotted on a polyvinylidene difluoride (PVDF) membrane. The resulting fraction is blocked with PBS containing 1% bovine serum albumin (BSA) (hereinafter referred to as "BSA solution"), and is then reacted with from 1 to 10 μg/ml of the anti-RNR·R2 subunit monoclonal antibody obtained in (4) at room temperature for 2 hours or at 4° C. for 10 hours. The reaction mixture-containing EIA plate is washed well with PBS or PBS-Tween. Subsequently, 1 to 50 μg/ml of an anti-mouse immunoglobulin antibody or an anti-rat immunoglobulin antibody labeled with biotin, an enzyme, a chemiluminescent substance or a radioactive compound is distributed in an amount of 50 to 100 μl/well as a second antibody, and the reaction is conducted at room temperature for 1 to 2 hours. The resulting mixture is washed well, and the reaction is conducted depending on the labelling compound for the second antibody. It is confirmed that the anti-RNR·R2 subunit monoclonal antibody is reacted with a protein having a molecular weight of 45K daltons which coincides with the molecular weight of the RNR·R2 subunit.

(6) Examination of specificity of the monoclonal antibody by the immunoprecipitation The reaction specificity of the anti-RNR·R2 subunit monoclonal antibody obtained in (4) is examined by the following immunoprecipitation.

The purified monoclonal antibody obtained in (4) and a control antibody (each of 5 to 50 μg/ml) are added to an EIA plate in an amount of 50 to 200 μl/well, allowed to stand for 10 hours at 4° C. and adsorbed on the plate. The EIA plate is washed three times with PBS, and a BSA solution is added thereto in an amount of 300 μl/well for blocking. The C-terminal peptide (100 μg/ml) of the R2 subunit of RNR or PBS is added thereto in an amount of 50 μl/well, and the reaction is conducted at room temperature for 2 hours. Subsequently, a crude fraction of RNR prepared from a human tumor cell line such as HelaS$_3$ is added thereto in an amount of 100 μl/well, and the reaction is conducted for 10 hours at 4° C. After the reaction mixture-containing EIA plate is washed with Tween-PBS, a sample buffer for SDS-PAGE (solution having a 5-time-concentration) is added thereto in an amount of 50 μl/well, and the mixture is shaken at room temperature for 2 hours. The reaction mixture is diluted by 5 times with PBS, and then fractionated through SDS-PAGE at a rate of 20 μl/lane. The fraction is then blotted on a PVDF membrane in the conventional manner. The blotted fraction is blocked with a BSA solution, and then reacted with 1 to 10 μg/ml of the purified anti-RNR·R2 subunit monoclonal antibody at room temperature for 2 hours. The reaction mixture-containing EIA plate is washed with Tween-PBS. An anti-mouse immunoglobulin antibody or an anti-rat immunoglobulin antibody (1 to 50 μg/ml) labeled with biotin, an enzyme, a chemifluorescent substance or a radioactive compound is added thereto as a second antibody, and the reaction is conducted at room temperature for 1 to 2 hours. The reaction mixture-containing EIA plate is washed well with PBS containing 0.02% Tween. The reaction corresponding to the labeled second antibody is then conducted, and it is confirmed that the anti-RNR·R2 subunit monoclonal antibody precipitates a protein having a molecular weight of 45K daltons which coincides with the molecular weight of the R2 subunit of RNR.

(7) Examination of RNR-inhibiting activity using the monoclonal antibody

Whether or not the anti-RNR·R2 subunit monoclonal antibody can inhibit RNR activity can be judged by determining an amount of deoxy cytidine 5'-diphosphate (CDP) converted from CDP through the RNR crude fraction derived from P388 cells.

The purified monoclonal antibody of the anti-RNR·R2 subunit obtained in (4) is diluted stepwise, and distributed into wells. An RNR crude fraction derived from P388 cells which has been prepared in the same manner as in (5) is added thereto, and the mixture is reacted at 4° C. for 1 to 2 hours. A solution containing CDP labeled with tritium is added thereto, and the reaction is conducted at 37° C. for 30 minutes. Thereafter, the reaction mixture is heated at 95° C. for 2 minutes to stop the reaction. Further, a snake venom derived from *Crotalus adamanteus* is added thereto, and the mixture is incubated at 37° C. for 2 hours. After the nucleotide is converted to the nucleoside, the mixture is centrifuged, and the supernatant is spotted on a polyethyleneimine (PEI)-borate-cellulose sheet. The substance is developed using a developing solvent (mixture of 20 mM ammonium formate and ethanol at a ratio of 6:4), and dried.

Then, the portions corresponding to the nucleoside and the deoxynucleoside are cut out, and the radioactivity is measured using a liquid scintillation counter.

(8) Immunocytochemical staining using the monoclonal antibody

Suspended cells are put on a plate as such. Adherent cells are peeled off using trypsin EDTA (PBS containing 0.1% trypsin and 0.02% EDTA), and are then put on the plate. At that time, the amount of the cells is $1 \times 10^6$ cells/well. The cells are washed with PBS, and 4% paraformaldehyde prepared just before use, is added thereto in an amount of 100 to 500 μl/well. The mixture is allowed to stand at room temperature for 30 minutes, and fixed. After the mixture is washed with PBS, methanol is added thereto in an amount of 100 to 500 μl/well in order to increase the antibody permeability of the cell membrane, and the treatment is conducted at $-20°$ C. for 2 minutes. After the thus-treated substance is washed with PBS, 10% normal human serum is added thereto in an amount of 100 to 500 μl/well, and the blocking is conducted at room temperature for 30 minutes. Subsequently, 1 to 10 μg/ml of the purified anti-RNR·R2 submit monoclonal antibody obtained in (4) is added thereto, and the reaction is conducted at room temperature for 30 minutes. After the reaction mixture-containing EIA plate is washed with PBS, 1 to 50 μg/ml of an anti-mouse immunoglobulin antibody or an anti-rat immunoglobulin antibody labeled with a fluorescent pigment such as FITC is added in an amount of 100 to 500 μl/well. The reaction is conducted at 4° C. for 30 minutes while shielding the light. After the completion of the reaction, the reaction mixture is washed well with PBS, and then analyzed by means of a cell sorter.

When the double staining of antibody staining and DNA staining is conducted, the antibody staining is conducted as mentioned above, and PBS containing 0.25 mg/ml of ribonuclease (RNase, made by Sigma Co.) and 0.1% NP40 is added in an amount of 0.9 ml per $1 \times 10^6$ cells, and the reaction is carried out at 37° C. for 30 minutes. Further, PBS containing 500 μg/ml of PI (propium iodide) and 1.0% NP40 is added thereto in an amount of 0.1 ml per $1 \times 10^6$ cells, and the reaction is carried out for 20 minutes or longer while cooling the mixture with ice. The reaction mixture is analyzed by means of a cell sorter.

(9) Immunohistochemical staining using the monoclonal antibody

A formalin-immobilized paraffin-embedded human tissue is sliced to a thickness of 1 to 5 microns, and is fixed on an egg-albumin-coated slide glass. The paraffin is removed with xylene, and the residue is rendered hydrophilic stepwise with a mixture of alcohol and water. In the case of using a frozen slice, the tissue is fixed in cold acetone for 20 minutes. Subsequently, the thus-treated slice is treated with methanol containing 0.3% hydrogen peroxide for 30 minutes to block internal peroxidase. The slice is washed with PBS, then blocked in a diluted normal horse serum for 20 minutes, and reacted with 1 to 10 μg/ml of the purified monoclonal antibody of RNR·R2 subunit obtained in (4) at 4° C. for 12 hours. After the reaction mixture-containing EIA plate is washed well, 1 to 50 μg/ml of an anti-mouse immunoglobulin antibody or an anti-rat immunoglobulin antibody labeled with biotin, an enzyme, a chemifluorescent substance or a radioactive compound is added thereto as the second antibody, and the reaction is conducted at room temperature for 30 minutes. After the reaction mixture-containing EIA plate is washed, the reaction corresponding to the labeled second antibody is conducted. After the reaction is stopped by cooling the reaction mixture with ice, the formalin-immobilized paraffin-embedded tissue is stained with hematoxylin, dehydrated with a mixture of alcohol and water and with xylene, fixed with Canada balsam, and observed microscopically. In the case of using the frozen slice, the frozen slice is fixed with a mixture of glycerin and PBS, and observed microscopically.

The present invention is further embodied specifically by referring to the following Examples.

EXAMPLE 1

(1) Preparation of an immunogen

A C-terminal peptide of a R2 subunit of human RNR having an amino acid sequence shown in SEQ. ID NO:1 was synthesized. A conjugate of the peptide with KLH (made by Carbiochem) was prepared in order to increase the immunogenicity, and was used as an immunogen.

KLH was dissolved in PBS to a concentration of 10 mg/ml, and MBS (made by Nacalai Tesque Co.) was added dropwise in an amount of 25 mg/ml which was 1/10 based on the amount of the solution. The reaction was conducted for 30 minutes. Free MBS was removed using a Sephadex G-25 column (manufactured by Pharmacia Co.) which had been equilibrated with PBS, and 2.5 mg of the resulting KLH-MBS was mixed with 1 mg of the C-terminal peptide of the R2 subunit of human RNR dissolved in a 0.1M sodium phosphate buffer (pH 7.0). The mixture was allowed to stand at room temperature for 3 hours with stirring. After the completion of the reaction, the reaction mixture was dialyzed against PBS containing 0.5M sodium chloride, and the resulting dialyzate was used as an immunogen.

(2) Immunization of an animal and preparation of antibody-producing cells

100 μg of the conjugate of the C-terminal peptide of the R2 subunit of human RNR and KLH obtained in (1) was administered to each of 5-week-old SD-strain male rats together with 2 mg of aluminum gel and $1 \times 10^9$ cells of Pertussis vaccine (made by Serum Institute, Chiba Prefecture). Two weeks later, 100 μg of the above-mentioned conjugate was administered once a week, in a total of 4 times. The blood was collected from the eyeground venous plexus, and the serum antibody titer thereof was determined through enzyme immunoassay. From the rat that exhibited the sufficient antibody titer, the spleen was extracted three days after the final immunization.

The spleen was cut into pieces in MEM (made by Nissui Pharmaceutical), loosened by means of a pincette, and centrifuged at 1,200 rpm for 5 minutes. The supernatant was discarded, and the residue was treated with a tris-ammonium phosphate buffer (pH 7.65) for 1 to 2 minutes to remove the red blood cells. The residue was washed three times with MEM, and used for cell fusion.

Enzyme immunoassay

A thyroglobulin (THY) conjugate of the C-terminal peptide of the human RNR·R2 subunit was prepared as an antigen for enzyme immunoassay by a glutaraldehyde method as follows.

1 mg of the C-terminal peptide of the human RNR·R2 subunit was dissolved in a 0.1M ammonium acetate buffer, and 5 mg of THY dissolved in the same buffer was added thereto until the total amount was 1 ml. While stirring the mixture, 540 μl of 0.02M glutaraldehyde was added dropwise thereto. The mixture was stirred at room temperature for 5 hours. After the completion of the reaction, the reaction mixture was dialyzed against PBS for 10 hours, and the resulting dialyzate was used as an antigen.

On a 96-well EIA plate (manufactured by Gleiner), 10 μg/ml of the thus-obtained C-terminal peptide conjugate of THY-human RNR·R2 subunit and THY-SOX47-3

(conjugate of SOX47-3 peptide and THY; an amino acid sequence of SOX47-3 was shown in Sequence No. 2) as a control antigen were distributed in 50 μl/well, allowed to stand for 10 hours at 4° C., and adsorbed on the plate. After the EIA plate was washed with PBS, 1% BSA-PBS was added thereto in 100 μl/well, and the reaction was conducted at room temperature for one hour to block the remaining active group. 1% BSA-PBS was discarded, and the supernatant of the hybridoma culture or an anti-serum of an immunized rat was distributed in 50 μl/well. The reaction was conducted for 2 hours. After the reaction mixture was washed with Tween-PBS, a peroxidase-labeled rabbit anti-rat immunoglobulin (made by Dako) was added thereto in 50 μl/well. The reaction was conducted at room temperature for 1 hour. After the EIA plate was washed with Tween-PBS, an ABTS substrate solution [ammonium 2.2-azinobis(3-ethylbenzothiazole-6-sulfonate)] was applied and the color developed was determined using the absorbance OD415 nm (NJ2001, manufactured by Nippon Intermed K.K.).

(3) Preparation of myeloma cells

8-Azaguanine-resistant murine myeloma cell line P3-U1 was cultured in normal medium to obtain at least $2 \times 10^7$ cells at the time of the cell fusion, and submitted to the cell fusion as a parent strain.

(4) Hybridoma production

The mouse spleen cells and myeloma cells obtained in (2) and (3) were mixed at a ratio of 10:1, and the mixture was centrifuged at 1,200 rpm for 5 minutes. Then, the supernatant was discarded, and the pellet was suspended thoroughly. Subsequently, a mixed solution containing 2 g of polyethylene glycol-1,000 (PEG-1,000), 2 ml of MEM and 0.7 ml of dimethyl sulfoxide was added thereto at 37° C. in an amount of 0.2 to 1 ml per $1 \times 10^8$ mouse spleen cells with stirring, and 1 to 2 ml of MEM was added thereto several times every 1 to 2 minutes. Further, MEM was added until the total amount was 50 ml. After the mixture was centrifuged at 900 rpm for 5 minutes, the supernatant was discarded, and the cells were gently suspended. Then, the cells were slowly suspended in 100 ml of HAT medium while the cells were sucked in and out by means of a measuring pipette.

Figure 1:
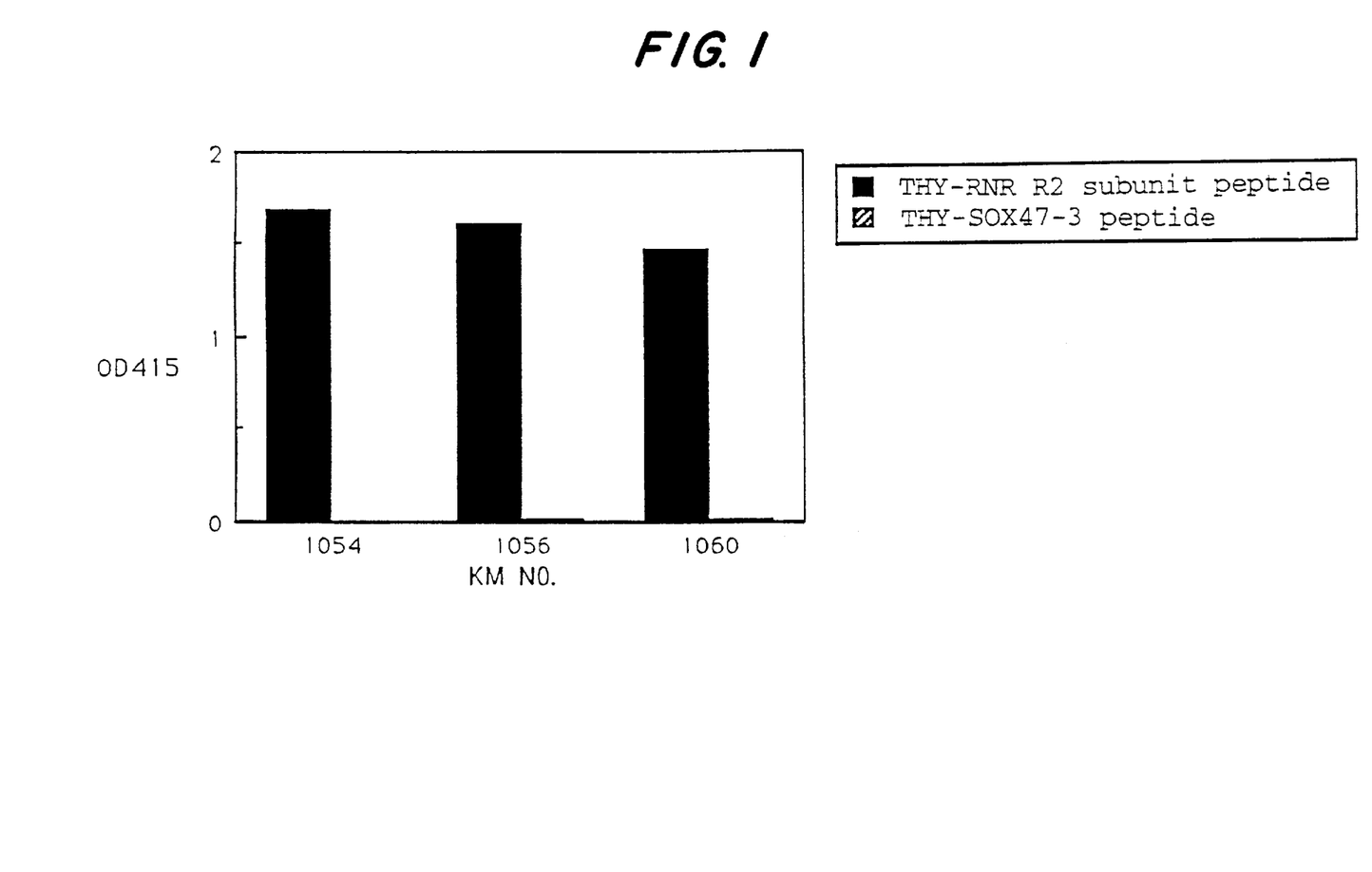
FIG. 1 is a graph showing the reactivity when anti-RNR·R2 subunit monoclonal antibodies KM1054, KM1056 and KM1060 were reactive with the C-terminal peptide of the R2 subunit in the enzyme immunoassay.

The suspension was distributed on a 96-well plate for cultivation in an amount of 100 μl/well, and incubated in a 5% $CO_2$ incubator at 37° C. for 10 to 14 days. The titer of the culture supernatant was determined through the above-mentioned enzyme immunoassay, and the well in which the specific reactivity with the R2 subunit C-terminal peptide of RNR was higher, was selected. The HAT medium was replaced with an HT medium and normal medium, and the cloning was repeated twice to obtain a hybridoma cell line producing the anti-RNR·R2 subunit monoclonal antibody. As a result, hybridoma KM1054, KM1056 and KM1060 were selected as shown in FIG. 1. The antibody classes of the monoclonal antibodies produced by the hybridomas were determined through the enzyme immunoassay using a subclass typing kit. The results are shown in Table 1.

TABLE 1

| KM No. | Antibody class |
|---|---|
| 1054 | IgG2a |
| 1056 | IgG2a |
| 1060 | IgG2a |

(5) Purification of the monoclonal antibody

At a dose of 5 to $20 \times 10^6$ cells/mouse, the hybridoma obtained in (4) was intraperitoneally injected into pristane-treated 8-week-old nude female mice (Balb/c). In 10 to 21 days, the hybridoma produced ascites carcinoma. The ascitic fluid was collected from ascitic fluid-bearing mice (1–8 ml/mouse), and was centrifuged at 3,000 rpm for 5 minutes to remove the solids. The residue was purified by the capric acid precipitation method (Antibodies-A Laboratory Manual, Cold Spring Harbor Laboratory, 1988) to obtain a purified monoclonal antibody.

(6) Examination of specificity of the monoclonal antibody through Western blotting An RNR crude fraction was prepared from $HelaS_3$ cells as follows.

$HelaS_3$ cells ($1 \times 10^9$) were suspended in 30 ml of a buffer capable of solubilizing cells comprising 20 mM Hepes (pH 7.6), 10 mM $MgCl_2$, 2 mM DTT and 1 mM PMSF, and the suspension was allowed to stand for 30 minutes on ice, and then it was homogenized. The homogenate was centrifuged at 35,000×g for 30 minutes to collect a supernatant. Streptomycin sulfate was added thereto until the final concentration reached 0.65% (w/v). The mixture was stirred at 4° C. for 30 minutes, and the reaction mixture was centrifuged at 13,000×g for 20 minutes to collect a supernatant. To the supernatant was added ammonium sulfate until the final concentration reached 50% saturation. The mixture was stirred at 4° C. for 45 minutes, and then centrifuged at 13,000×g for 20 minutes to obtain a pellet. The pellet was dissolved in 4 ml of a tris-hydrochloride buffer comprising 50 mM tris-hydrochloride (pH 7.6), 0.1 mM PMSF and 2 mM DTT, and the solution was further dialyzed for 10 hours against the above-mentioned buffer. The resulting dialyzate was used as an RNR crude fraction.

Figure 2:
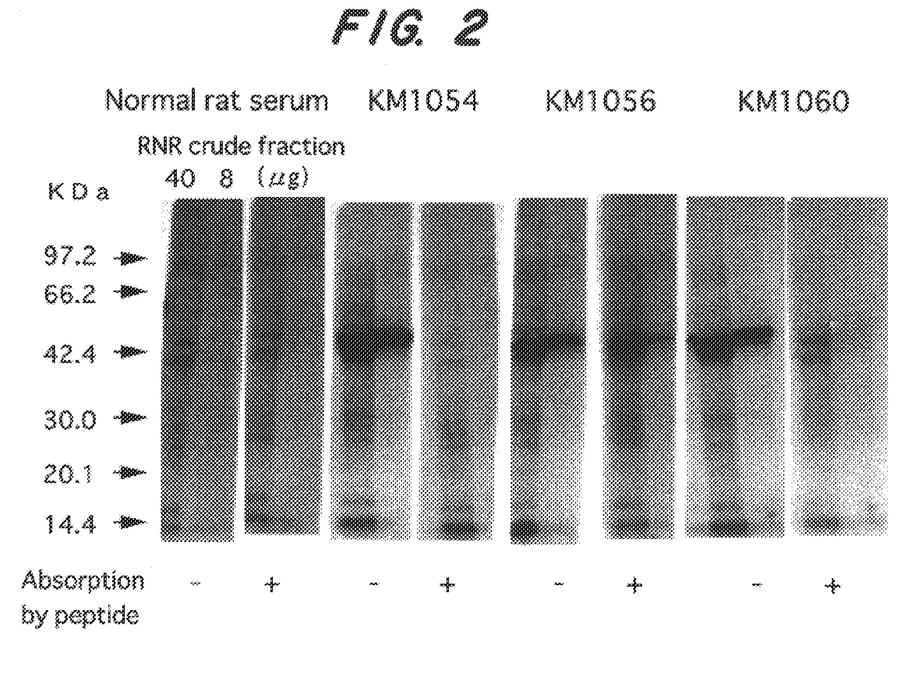
FIG. 2 shows the reactivity of the anti-RNR·R2 subunit monoclonal antibodies KM1054, KM1056 and KM1060 with the RNR crude fraction derived from HelaS$_3$ cells in Western blotting. In the drawing, + indicates reactivity when the antibody which had been reacted with the C-terminal peptide of the RNR·R2 subunit, was added, and – indicates the reactivity when the antibody was added as such.
Figure 3:
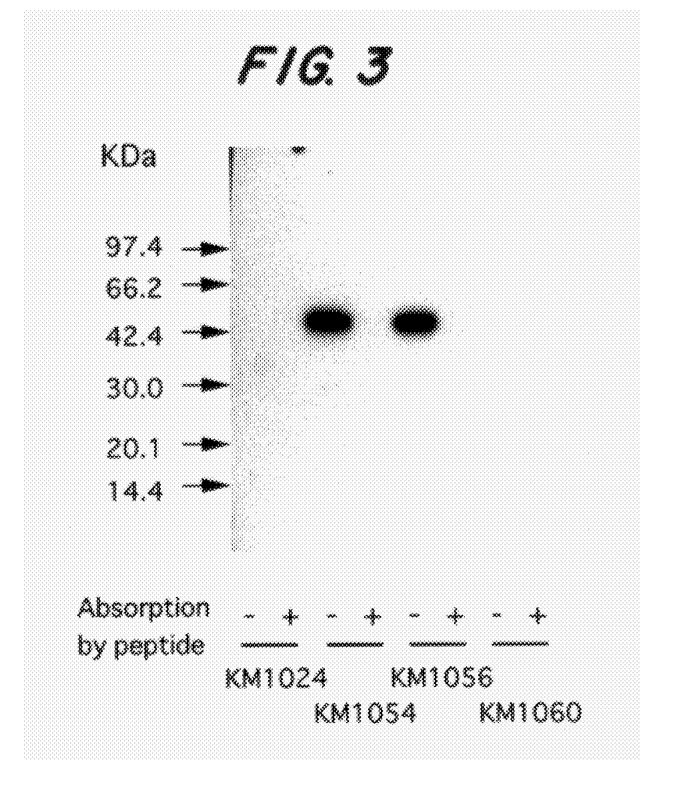
FIG. 3 shows the reactivity of the anti-RNR·R2 subunit monoclonal antibodies KM1054, KM1056 and KM1060 with the RNR crude fractions derived from HelaS$_3$ cells in the immunoprecipitation. In the drawing, + indicates the reactivity when the antibody which had been reacted with the C-terminal peptide of the RNR·R2 subunit was added, and – indicates the reactivity when the antibody was added as such.

The RNR crude fraction was fractionated through SDS-PAGE in an amount of 40 μg/lane or 8 μg/lane, and was blotted on a PVDF membrane in a conventional way. The fraction was blocked with 1% BSA-PBS, and then reacted with 10 μg/ml of each of the human RNR·R2 subunit monoclonal antibodies KM1054, KM1056 and KM1060 obtained in (5) and the normal rat serum (diluted to 500 times with 1% BSA-PBS) as a control antibody at room temperature for 2 hours or for 10 hours at 4° C. The fraction was also reacted with each of these antibodies which had been reacted with the RNR C-terminal peptide (final concentration 10 μg/ml) at room temperature for 1 hour. The EIA plate was washed well with Tween-PBS, and then reacted with a peroxidase-labeled anti-rat immunoglobulin antibody (Dako) at room temperature for 1 hour. The EIA plate was washed well with Tween-PBS, and the solution was then sucked up. An ECL (made by Amersham Co.) reagent was added thereto, and the mixture was allowed to stand for 1 minute. After the completion of the reaction, the excess reagent was removed, and the film was sensitized for 10 seconds to 2 minutes for detection. Consequently, as shown in FIG. 2, each of KM1054, KM1056 and KM1060 was reacted with a protein having a molecular weight of 45K daltons which coincides with the molecular weight of the RNR·R2 subunit, but the reactivity disappeared when the antibodies had been reacted with the RNR C-terminal peptide.

(7) Examination of specificity of the monoclonal antibody by immunoprecipitation The anti-RNR·R2 subunit monoclonal antibody KM1054, KM1056 and KM1060, and rat IgG antibody KM1024 (50 μg/ml) as a control was distributed in 200 μl/well, and adsorbed on the plate for 10 hours at 4° C. (The rat IgG antibody KM1024 is not publicly available. As the control, KM987 in place of KM1024 can be used, because KM987 is completely identical with KM1024. KM987 is described in the Journal of Biological Chemistry 268, 25846 (1993)). After the EIA plate was washed three times with PBS, 1% BSA-PBS was added in 300 μl/well, and the mixture was blocked at room temperature for 1 hour. 1% BSA-PBS was discarded, the RNR·R2 subunit C-terminal peptide (100 μg/ml) or PBS was added in 50 μl/well, and the mixture was allowed to stand at room temperature for 2 hours. Subsequently, the RNR crude fraction (7.67 mg/ml) was added in 100 μl/well, and the mixture was allowed to stand for 10 hours at 4° C. The EIA plate was washed with Tween-PBS, and a sample buffer for SDS-PAGE (containing 25% 2-mercaptoethanol solution, and concentrated to one-fifth) was added thereto in 50 μl/well. The mixture was shaken at room temperature for 2 hours, and the reaction mixture was diluted to 5 times with PBS, then fractionated through SDS-PAGE in 20 μl/lane, and blotted on a PVDF membrane in a conventional way. The fraction was blocked with 1% BSA-PBS, and then reacted with an antibody mixed solution (1% BSA-PBS solution containing each monoclonal antibody KM1054, KM1056, KM1060 or KM1024 in an amount of 10 μg/ml) at room temperature for 2 hours. The reaction mixture was washed with Tween-PBS, and a peroxidase-labeled rabbit anti-rat immunoglobulin (made by Dako) was added thereto. The mixture was allowed to stand at room temperature for 1 hour. In the same way as in (6), the reaction was conducted using the ECL reagent (Amersham) for the detection. As a result, monoclonal antibodies of KM1054 and KM1056 precipitated a protein having a molecular weight of 45K daltons which coincides with the molecular weight of the RNR·R2 subunit, and the reactivity when the antibodies had been reacted with the R2 subunit C-terminal peptide, disappeared.

(8) RNR-inhibiting activity using the monoclonal antibody

Whether or not the anti-RNR·R2 subunit monoclonal antibody can inhibit RNR activity was examined using as an index an amount of deoxy CDP converted from CDP through the RNR crude fraction derived from P388 cells.

Figure 4:
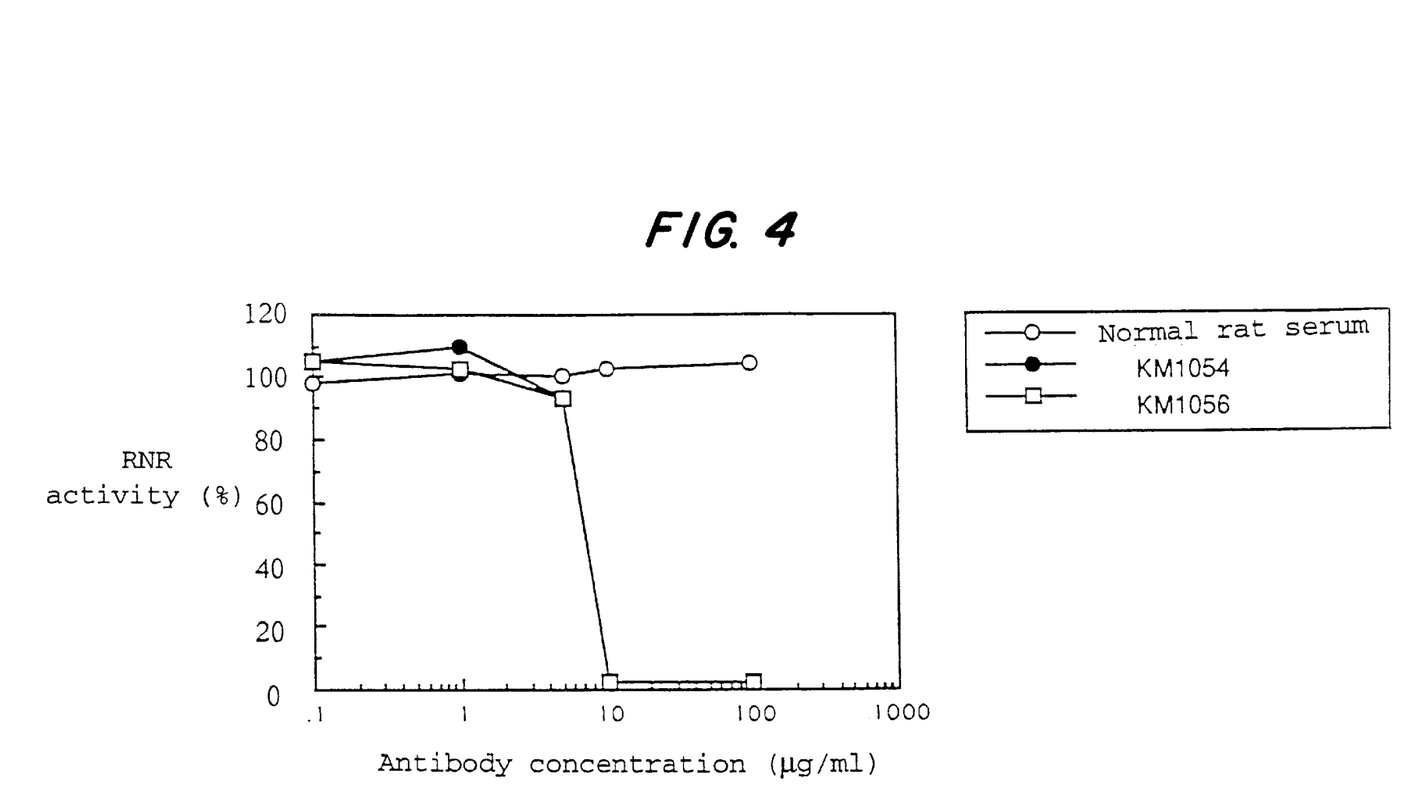
FIG. 4 is a graph showing the RNR-inhibiting activity of the anti-RNR·R2 subunit monoclonal antibodies KM1054 and KM1056.
Figure 5A:
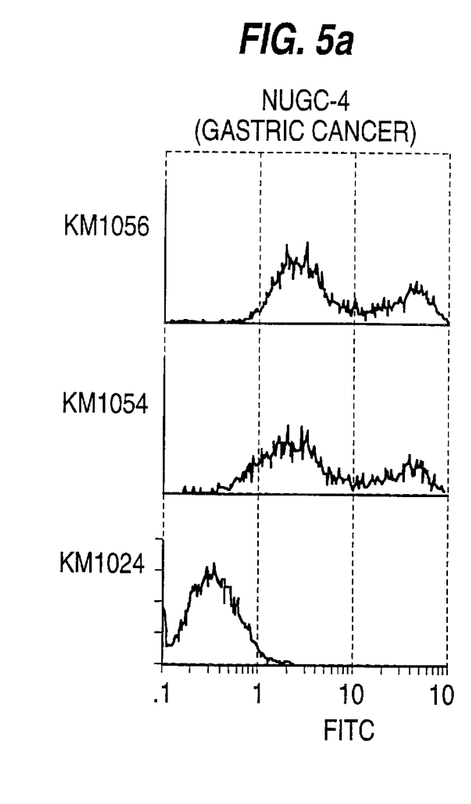
FIGS. 5a–5d shows the results given when analyzing the reactivities of the anti-RNR·R2 subunit monoclonal antibodies KM1054 and KM1056 and anti-wortmannin monoclonal antibody KM1024 with various cancer cells NUGC-4, TPC-1, Calu-1 and U937 respectively in the immunocyte staining by means of a cell sorter.
Figure 5B:
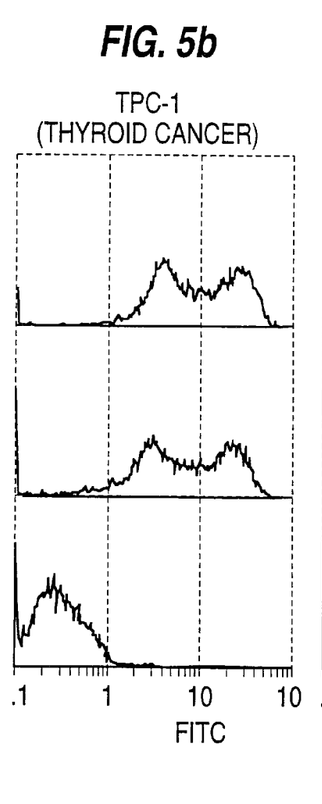
Figure 5C:
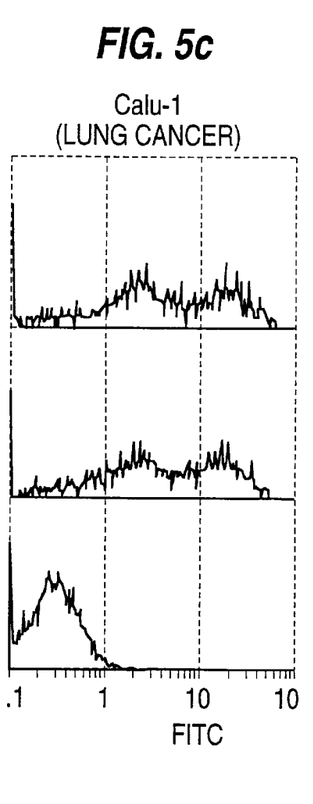
Figure 5D:
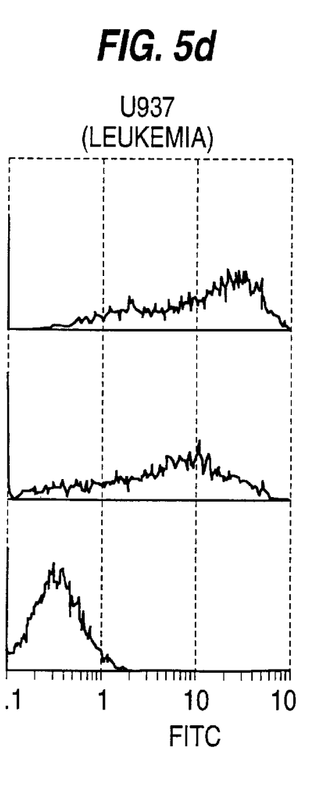

The purified anti-RNR·R2 subunit monoclonal antibodies KM1054 and KM1056 obtained in (5) were diluted stepwise to 0.1 to 100 μg/ml. Subsequently, 50 μl of each of the thus-obtained diluted monoclonal antibodies was mixed with 0.75 mg/50 μl of an RNR crude fraction derived from P388 cells. The mixture was allowed to stand at 4° C. for 1 to 2 hours, and 25 μl of a substrate solution containing tritium-labeled CDP [solution comprising 5 mM ATP, 5 mM MgCl$_2$, 50 mM Hepes (pH 7.4), 5 mM DTT, 10 mM NaF, 0.5 mM CDP and 1.25-μCi $^3$H-CDP] was add, and the mixture was allowed to stand at 37° C. for 30 minutes. Subsequently, the reaction mixture was heated at 95° C. for 2 minutes to stop the reaction. Further, 20 mg/ml of a snake venom derived from *Crotalus adamanteus* was added thereto in 25 μl/well, and the mixture was incubated at 37° C. for 2 hours to convert a nucleotide to a nucleoside. The thus-obtained reaction mixture was heated at 95° C. for 2 minutes to stop the reaction. The reaction mixture was centrifuged at 5,000 rpm for 2 minutes. 10 μl of the thus-obtained supernatant was spotted on a polyethyleneimine (PEI)-borate-cellulose sheet, and developed in a developing buffer (a 6:4 mixture of 20 mM ammonium formate and ethanol), and dried. Thereafter, the portions corresponding to the nucleoside and the deoxynucleoside were cut out, and the radioactivity thereof was measured using a liquid scintillation counter. Consequently, monoclonal antibodies KM1054 an d KM1056 inhibited the RNR activity depending on the antibody concentration as shown in FIG. 4.

EXAMPLE 2

(1) Reactivity of the monoclonal antibody with cancer cells

The reactivity of monoclonal antibodies KM1054 and KM1056 obtained in Example 1 with various cancer cells was examined as follows.

Human gastric cancer cell line NUGC-4, human thyroid cancer cell line TPC-1, human lung cancer Calu-1 (ATCC HTB54) and human leukemia cell line U937 (ATCC CRL1593) were used as cancer cells. Suspended cells were put on a plate as such, and adherent cells were peeled off using trypsin EDTA, and were put on the plate. At this time, the amounts of these cells were 1×10$^6$ cells/well. The cells were washed with PBS, and 4% paraformaldehyde prepared just before use was added thereto in 500 μl/well. The mixture was allowed to stand at room temperature for 30 minutes, and fixed. The mixture was washed with PBS, and methanol was added thereto in 500 μl/well for the purpose of increase in the antibody permeability of the cell membrane, and the treatment was conducted at −20° C. for 2 minutes. The thus-treated substance was washed with PBS, and 10% normal human serum was added thereto in 500 μl/well, and the blocking was conducted at room temperature for 30 minutes. Subsequently, 10 μg/ml of monoclonal antibody KM1054, KM1056 or KM1024 each was added thereto in 200 μl/well, and the reaction was conducted at room temperature for 30 minutes. After the reaction mixture was washed with PBS, PBS was discarded, and an FITC-labeled anti-rat immunoglobulin antibody (made by Dako) was added in 200 μl/well. The reaction was conducted at 4° C. for 30 minutes while shielding the light. After the completion of the reaction, the reaction mixture was washed well with PBS, and then analyzed by cell sorter (Epics Elite manufactured by Coulter). As a result, as shown in FIG. 5, the monoclonal antibodies KM1054 and KM1056 were reacted with all of the cancer cell lines. Thus, it was shown that each antibody of KM1054 and KM1056 can be used to detect RNR which was scattered in the cancer cells.

(2) Reactivity of monoclonal antibodies with cell cycle

The double staining of antibody staining and DNA staining was conducted as follows in order to examine the relationship between the reactivity of the monoclonal antibodies KM1054 and KM1056 and the cell cycle.

The staining was conducted using (A) human-T-lymphocyte cell line CCRF-CEM (ATCC CCL119), and (B) lymphocytes collected from human peripheral blood by centrifugation using Polymorphprep (made by Daiichi Chemical Co.) and lymphocyte blasts obtained by stimulating the above-mentioned lymphocyte with OKT-3 which is a supernatant obtained by cultivating hybridoma OKT-3 (ATCC CRL8001) and purifying a culture using a protein A column, and IL-2 (made by Shionogi & Co., Ltd.).

Figure 6A:
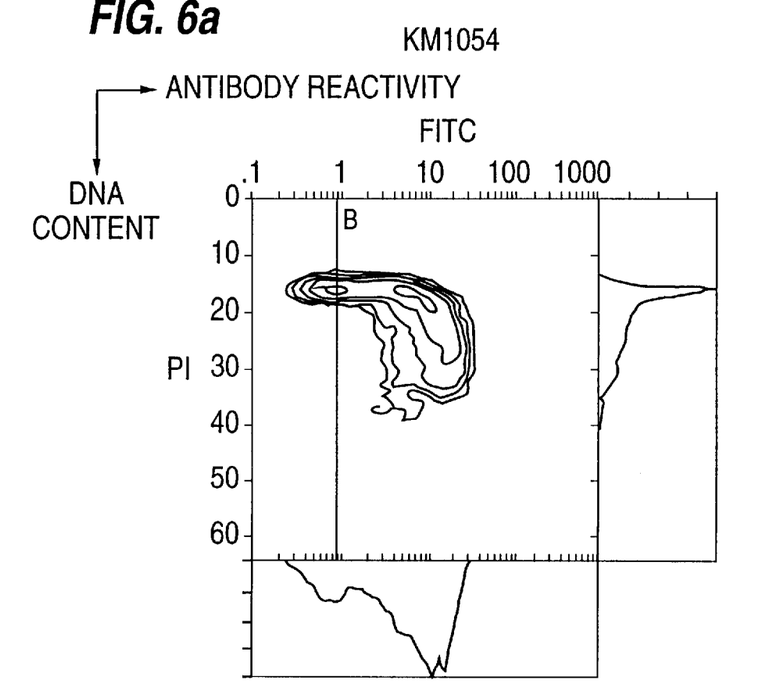
FIG. 6a shows the results given when the relationship of the reactivity of the anti-RNR·R2 subunit monoclonal antibody KM1054 and FIG. 6b shows the anti-wortmannin monoclonal antibody KM1024 with the cell cycle is analyzed by means of a cell sorter using human-T-cell lymphoma cell line CCRF-CEM.
Figure 6B:
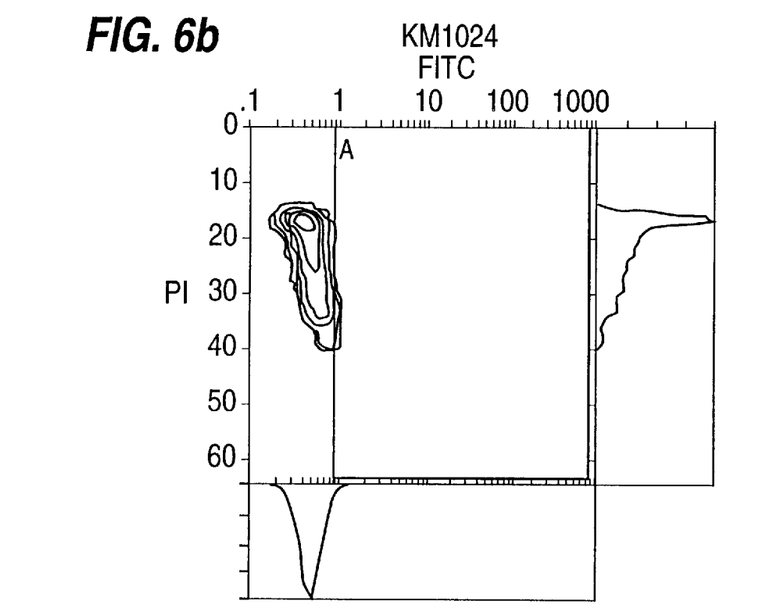
Figure 7A:
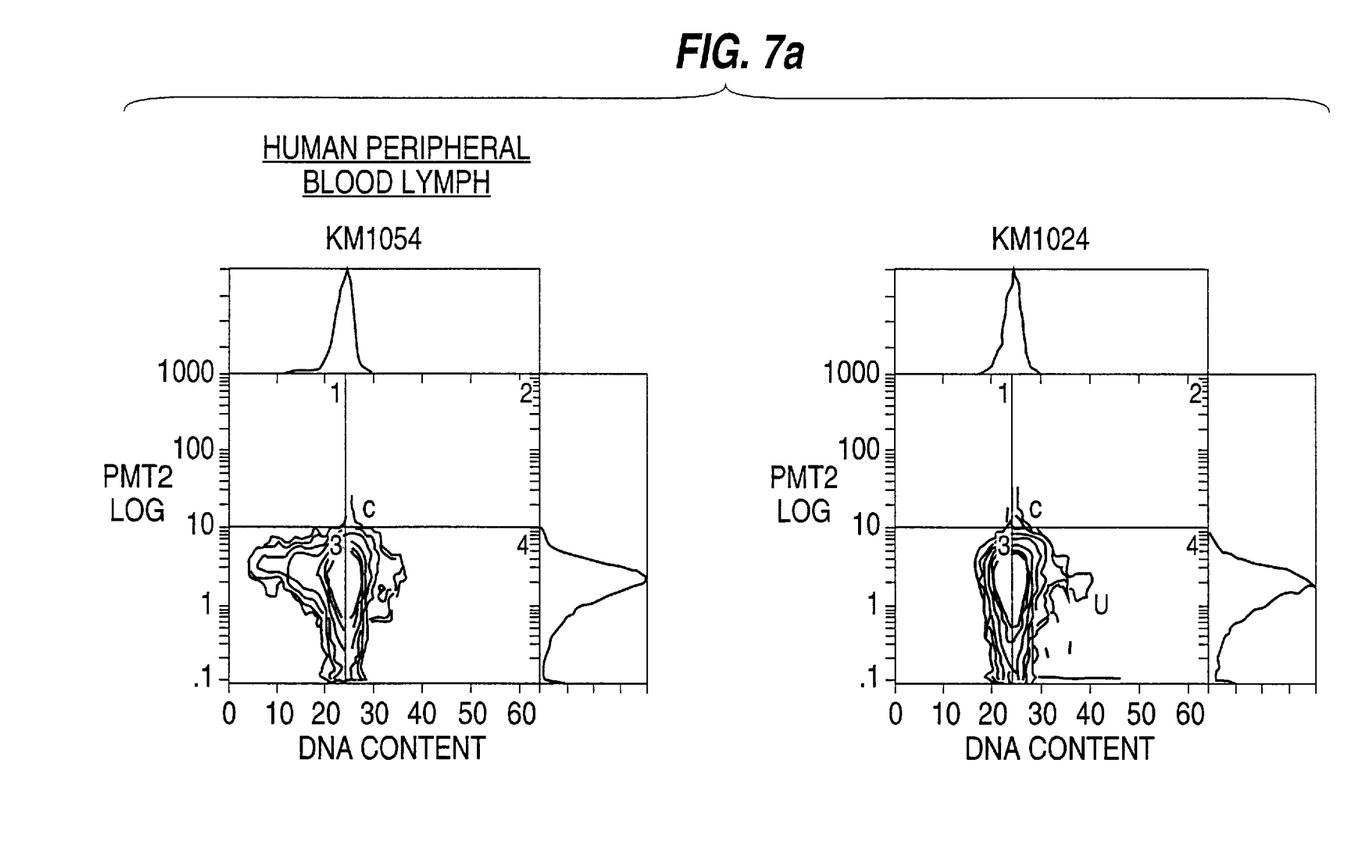
FIGS. 7a and 7b shows the results given when the relationship of the reactivity of the anti-RNR·R2 subunit monoclonal antibody KM1054 and the anti-wortmannin monoclonal antibody KM1024 with the cell cycle is analyzed by means of a cell sorter using human peripheral blood lymphocytes (FIG. 7a) and human peripheral blood lymphocytes blasts (FIG. 7b).
Figure 7B:
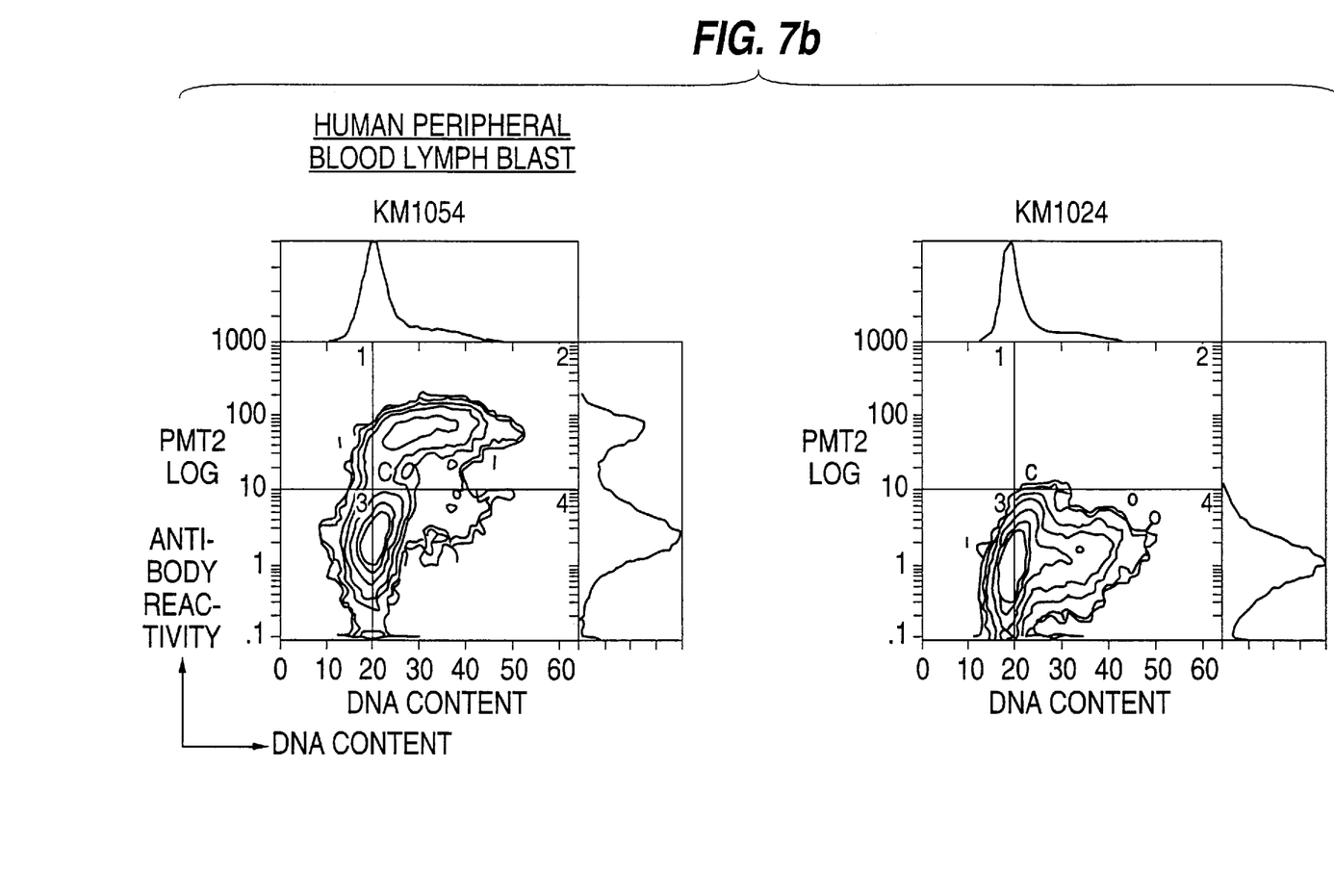

The antibody staining was conducted in the same method as in (1) using the monoclonal antibodies KM1054 and KM1024 as control. PBS containing 0.25 mg/ml of ribonuclease (RNase, made by Sigma Co.) and 0.1% NP40 was then added in 0.9 ml per 1×10$^6$ cells, and the reaction was carried out at 37° C. for 30 minutes. Further, PBS containing 500 μg/ml of PI (propium iodide) and 1.0% NP40 was added thereto in 0.1 ml per 1×10$^6$ cells, and the reaction was carried out for 20 minutes or longer on ice with stirring. The reaction mixture was analyzed by cell sorter (Epics Elite manufactured by Coulter). The results were shown in FIGS. 6 and 7. In case of using human-T-lymphocyte cell line CCRF-CEM, as shown in FIG. 6, the monoclonal antibody KM1054was reacted with a part of the cells at G1 phase as well as with cells at S phase, G2 phase and M phase. In case of using the unstimulated peripheral blood lymphocyte, as shown in FIG. 7, the monoclonal antibody KM1054 as well as the control antibody KM1024 were not reacted with the cells at G0 phase. In the lymphocyte blasts in which the lymphocytes grew synchronously using OKT-3 and IL-2, appearance of not only a population at G0/G1 phase but also populations at S phase, G2 phase and M phase were observed. The control antibody KM1024 was not reacted with any of these populations, and the monoclonal antibody KM1054 was selectively reacted with the populations at S phase, G2 phase and M phase, either of which has a high content of DNA.

Thus, the reactivity of the monoclonal antibody KM1054 coincided with the development of the RNR·R2 subunit dependent on the cell cycle, in which the level of RNR activity is lower at G0/G1 phase and higher at S phase, G2 phase and M phase. It was suggested that the monoclonal antibody KM1054 can be utilized to detect RNR which is useful as a cell cycle marker and a proliferation marker.

(3) Immunocytochemical staining using the monoclonal antibody

In order to examine the application of the anti-RNR·R2 subunit monoclonal antibody to cytodiagnosis, the following test was conducted: 5 ml of ascitic fluid cells or pleural fluid cells was collected from 3 samples of cancerous serositis, and immobilized using 95% ethanol. After the completion of the immobilization, the immunocytochemical staining was conducted using the monoclonal antibody KM1054 in the same way as in (1) except that ethanol was used instead of paraformaldehyde. As a result, all of the samples were positive as shown in Table 2.

TABLE 2

| Sample | Reactivity of KM1054 |
|---|---|
| C93-3034 ovarian cancer | + |
| C93-3325 ovarian cancer | + |
| C93-2845 breast cancer | + |

(4) Immunohistochemical staining using the monoclonal antibody.

A formalin-immobilized paraffin-embedded human tissue was sliced to a thickness of 1 to 5 microns, and was fixed on an egg-albumin-coated slide glass. The paraffin was removed with xylene, and the residue was then rendered hydrophilic stepwise with a mixture of alcohol and water. In case of using a frozen slice, the tissue was fixed in cold acetone for 20 minutes. Subsequently, the thus-treated slice was treated with methanol containing 0.3% hydrogen peroxide for 30 minutes to block internal peroxidase. The slice was washed with PBS, blocked in a diluted normal horse serum for 20 minutes, and reacted with 10 μg/ml of the purified RNR·R2 subunit monoclonal antibody at 40° C. for 12 hours. The reaction mixture was washed well with PBS, and 1 μg/ml of a biotin-labeled anti-rat immunoglobulin antibody (made by Jackson Immunoresearch Lab.) was added in 100 μl/well. The reaction was conducted at room temperature for 30 minutes. After the EIA plate was washed with PBS, an avidin-labeled peroxidase (made by Nichirei) was added thereto, and the mixture was reacted at room temperature for 30 minutes. The EIA plate was washed in water for 10 minutes, and then reacted with 0.05% diaminobenzidine containing 0.01% hydrogen peroxide for 1 minute. The reaction was stopped in cold water, and the reaction mixture was stained using hematoxylin. The formalin-immobilized paraffin-embedded tissue was dehydrated with a mixture of alcohol and water and with xylene, and the residue was fixed with Canada balsam, and observed microscopically. Consequently, as shown in Table 3, the monoclonal antibody KM1054 was reacted with the cancer cells in all of the eight breast cancer samples, but not with the surrounding normal portions and benign tumors (4 samples).

TABLE 3

| | | | Reactivity of KM1054 | |
|---|---|---|---|---|
| Sample No. | Histological view | Type of slice* | Cancer portion | Normal portion |
| 93-2638 | infiltration lactiferous duct cancer | F & P | ++ & + | – |
| 93-4244 | infiltration lactiferous duct cancer | F | ++ | – |
| 93-4405 | infiltration lactiferous duct cancer | F | ++ | – |
| 94-20 | infiltration lactiferous duct cancer | F | ++ | – |
| 94-681 | infiltration lactiferous duct cancer | F & P | +++ & +++ | – |
| 94-747 | infiltration lactiferous duct cancer | F | ++ | – |
| 94-2753 | infiltration lactiferous duct cancer | P | + | – |
| 94-2754 | infiltration lactiferous duct cancer | P | ++ | – |
| 94-1025 | lactiferous duct mammillary line tumor | F | – | – |
| 93-4441 | lactiferous duct mammillary line tumor | F | – | – |
| 94-1143 | fibroadenoma | F | – | – |
| 94-905 | lactiferous duct cystofibroma | F | – | – |

*F-frozen slice
P-formalin-immobilized paraffin-embedded slice

---

What we claim is:

1. An IgG2 a monoclonal antibody KM1054 which is produced by the hybridoma cell line FERM BP-4875, specifically binds to a human ribonucleotide reductase R2 subunit and inhibits ribonucleotide reductase activity.

2. The monoclonal antibody as claimed in claim 1, which belongs to the IgG2a subclass, and is a rat monoclonal antibody.

3. Hydridoma cell line FERM BP-4875 producing the monoclonal antibody as in claim 1.

4. A method for in vitro detection of human ribonucleotide reductase R2 subunit using the monoclonal antibody as claimed in claim 1.

5. The method as claimed in claim 4, wherein the method is the immunohistochemical staining method.

6. The method as claimed in claim 4, wherein the method is the immunocytochemical staining method.

7. A method for in vitro detection the presence of human cancer cells using the monoclonal antibody as claimed in claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:1:

| Cys | Asn | Ser | Phe | Thr | Leu | Asp | Ala | Asp | Phe |
|---|---|---|---|---|---|---|---|---|---|
| 1 | | | | 5 | | | | | 10 |

(2) INFORMATION FOR SEQ ID NO:2:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:2:

| Cys | Leu | Ser | Pro | Gly | Gln | Lys | Gln | Lys | Glu | Glu | Pro | Lys | Glu | Val | Lys |
|---|---|---|---|---|---|---|---|---|---|---|---|---|---|---|---|
| 1 | | | | 5 | | | | | 10 | | | | | 15 | |